(12) United States Patent
Aoyagi

(10) Patent No.: US 6,858,181 B2
(45) Date of Patent: Feb. 22, 2005

(54) METHOD FOR CLEANING AND STERILIZING MEDICAL EQUIPMENT AFTER USE

(75) Inventor: Kohei Aoyagi, Tokyo (JP)

(73) Assignee: Kabushiki Kaisha Sunseal, Osaka-fu (JP)

(*) Notice: Subject to any disclaimer, the term of this patent is extended or adjusted under 35 U.S.C. 154(b) by 49 days.

(21) Appl. No.: 10/347,760

(22) Filed: Jan. 21, 2003

(65) Prior Publication Data

US 2003/0136426 A1 Jul. 24, 2003

(30) Foreign Application Priority Data

Jan. 22, 2002 (JP) .......................... 2002-012752
Dec. 27, 2002 (JP) .......................... 2002-379372

(51) Int. Cl.$^7$ .............. A61L 2/00; A62B 7/08; B08B 6/00; B08B 7/04; B08B 3/00
(52) U.S. Cl. .............. 422/24; 422/1; 422/20; 422/28; 422/120; 422/128; 422/292; 422/305; 134/1; 134/1.3; 134/184; 134/18; 134/113; 134/57 R; 134/26
(58) Field of Search ................ 422/1, 20, 24, 422/28, 32, 37, 40, 120, 128, 292, 305; 134/1, 1.3, 184, 18, 113.57 R, 26–30, 113, 57 R

(56) References Cited

U.S. PATENT DOCUMENTS

| | | | | |
|---|---|---|---|---|
| 4,868,397 A | * | 9/1989 | Tittel | ............ 250/455.11 |
| 4,943,414 A | * | 7/1990 | Jacobs et al. | |
| 5,696,046 A | * | 12/1997 | Green | |
| 5,792,422 A | * | 8/1998 | Lin et al. | |
| 5,868,667 A | * | 2/1999 | Lin et al. | |
| 6,042,802 A | * | 3/2000 | Drake | |
| 6,454,874 B1 | * | 9/2002 | Jacobs et al. | |
| 6,494,222 B1 | * | 12/2002 | Mitsumori et al. | |
| 6,555,053 B1 | * | 4/2003 | Aoyagi | |

* cited by examiner

Primary Examiner—Terrence R. Tm
Assistant Examiner—Monzer R. Chorbaji
(74) Attorney, Agent, or Firm—Dennis G. LaPointe; Mason Law, P.L.

(57) ABSTRACT

According to the present invention, a pre-cleaning process is performed for removing a physical substance such as blood, mucus or tiny pieces of tissue that are attached to the exterior of the medical device and are inside a duct or a hollow portion. Then, the pre-cleaned medical device is immersed in a chlorine dioxide solution and/or a chlorine dioxide solution is passed through the duct or the hollow portion. Thereafter, the medical device is placed in a chlorine dioxide gas atmosphere and/or a chlorine dioxide gas is passed through the duct or the hollow portion. In this manner, the exterior of the medical device and the interiors of the duct and the hollow portion are deodorized, disinfected and sterilized.

24 Claims, 3 Drawing Sheets

METHOD FOR CLEANING AND STERILIZING MEDICAL EQUIPMENT AFTER USE

BACKGROUND OF THE INVENTION

1. Field of the Invention

The present invention relates to a method for cleaning and sterilizing medical equipment after use. The target objects for this invention are fiberscopes, such as gastrocameras and other types of endoscopes, including peritoneoscopes, thoracoscopes and arthoroscopes, and medical supplies, such as catheters and tubes, that have long ducts or hollow portions and that tend to be repetitively employed by being introduced into human bodies.

2. Related Arts

Because of the need to prevent nosocomial bacterial or viral infections and mechanical accidents, and for economic reasons, inexpensive medical products, such as syringes, hypodermic needles and instillators, in most cases are classified as disposable materiel and are used only once and then discarded as infective waste. However, fiberscopes such as gastrocameras and other types of endoscopes, including peritoneoscopes, thoracoscopes and arthoroscopes, and other expensive medical products, like catheters and similar intubation equipment, must in principle be employed repetitively. And due to the necessity to prevent infection, each time these medical devices are used they must be thoroughly cleaned by hand, or in an automatic washer, and must thereafter be dried, deodorized and sterilized.

This type of medical equipment, epitomized by a fiberscope having a hollow portion or a narrow duct (a channel) that serves as a flow path for mucus or fluids or as an insertion path for forceps, for example, is a device that is extremely difficult to thoroughly clean and disinfect. Traditionally, to clean, deodorize, and sterilize such a medical device, the subsequently described disinfection and sterilization method has been widely employed. According to this method, ultrasonic cleaning is employed to clean the exterior surface of a device, and various types of cleaning fluids are used, as needed, to clean the inner wall of a duct or a hollow portion. Then, the device is sterilized by wiping it with ethanol, employed as a disinfectant, a fourth ammonium disinfectant, an iodine disinfectant or an aldehyde disinfectant, or by being immersed in various types of disinfectants, or gas sterilization is used for which the device is retained in a closed atmosphere, such as formalin gas or ethylene oxide gas.

According to this method, however, an extended time is required for deodorization and sterilization, so that a device for which such processing is performed can not be used frequently. Further, when a complicated cleaning device is employed, costs involved in its use are greatly increased. Other available methods are EOG sterilization and thermal sterilization, for which an autoclave is used; however, it is known that with these methods sterilization failures occur when air remains in a duct or a hollow portion. As a result, there is a demand for a drying, deodorization and sterilization method and apparatus that can safely, easily and completely deodorize and sterilize medical devices such as are described above.

To this end, it is well known that a chlorine dioxide solution, or gas, has a strong bleaching action and is an appropriate deodorization and sterilization agent, and many manufacturing methods have been proposed for employing this agent.

However, industrially produced high-density chlorine dioxide is a strong oxidizing agent, and can react with other materials and generate high-density chlorine. Further, it presents a slight possibility of an explosion. Because of these properties, a 5% solution of "stabilized chlorine dioxide", developed by International Dioxide Inc., has been provided as a chlorine dioxide that is less dangerous and easier to handle. This solution may be employed as a chlorine dioxide solution after it has been diluted, as needed, to a proper density.

A safe chlorine dioxide gas, which has no sharp or pungent odor, is obtained by vaporizing stabilized chlorine dioxide, and when brought into contact with a target device, provides various effects, including excellent deodorization, disinfection and sterilization. With this gas, the pasteurization of various viruses, bacteria, molds and pathogens and sterilization are performed extremely effectively, and can be completed within a short period of time. Further, great deodorization effects are also obtained, and chemical product and putrefaction odors are effectively removed. Further, the propagation of microorganisms that cause bad odors can be prevented.

As a deodorization and disinfection method and apparatus that use chlorine dioxide, proposed are a method and an apparatus (Japanese Unexamined Patent Publication No. 2002-306577) wherein an object to be disinfected is placed in a closed space, and is deodorized and disinfected by spraying a chlorine dioxide solution mist into this space. When this process is employed, however, it is difficult to completely deodorize and disinfect a medical device that has a duct or a hollow portion.

The present inventor has also proposed a method and an apparatus for providing the above effects by irradiating a gel of a stabilized dioxide solution with an ultraviolet beam to supply a deodorization and sterilization gas (Japanese Unexamined Patent Publication No. 2000-202009); and a method whereby a target device is immersed in a stabilized chlorine dioxide solution in a container that is filled with a gas generated from the stabilized chlorine dioxide, so as to deodorize and sterilize the object retained in the container (Japanese Unexamined Patent Publication No. 2001-29440). However, with these methods it is also difficult to deodorize and disinfect a medical device that has been used and that has a duct or a hollow portion. The present inventor, therefore, studied and conducted experiments to devise a method for cleaning, deodorizing and sterilizing medical devices after use, such as gastrocameras and other endoscopes, that have long ducts or hollow portions, and finally is able to provide the present invention.

SUMMARY OF THE INVENTION

Objects

It is a first object of the present invention to provide a cleaning, sterilization and deodorization method for medical devices that are repetitively used, whereby a medical device, after being used, can be efficiently cleaned, deodorized and sterilized with in a short period of time, by specifically employing either a chlorine dioxide solution or a chlorine dioxide gas that provides a highly effective sterilization action, or by generating ultrasonic vibrations in a chlorine dioxide solution.

It is a second object of the present invention to provide a method whereby medical devices can be efficiently cleaned, deodorized and sterilized after use by sequentially using both a chlorine dioxide solution and a chlorine dioxide gas that provide highly effective sterilization actions.

Summary

According to a first aspect of the present invention, a cleaning and sterilization method for medical devices after use comprises the steps of:

pre-cleaning, using detergent water, a medical device to be introduced into a human body; and bringing the medical device into contact with a chlorine dioxide solution and/or a chlorine dioxide gas, so that the exterior of the medical device and the inside of a duct or a hollow portion in the medical device are cleaned, disinfected and sterilized.

According to a second aspect of the present invention, a cleaning and sterilization method for medical devices after use comprises the steps of:

pre-cleaning the medical device using detergent water; and immersing the medical device in a chlorine dioxide solution and/or passing a chlorine dioxide solution through a duct or a hollow portion, or immersing the medical device in a chlorine dioxide solution and generating ultrasonic vibration, so that the exterior of the medical device and the inside of the duct or the hollow portion are cleaned, disinfected and sterilized.

According to a third aspect of the present invention, a cleaning and sterilization method for medical devices after use comprises the steps of:

pre-cleaning the medical device using detergent water; and placing the medical device in a chlorine dioxide gas atmosphere and/or passing a chlorine dioxide gas through a duct or a hollow portion, so that the exterior of the medical device and the inside of the duct or the hollow portion are cleaned, disinfected and sterilized.

According to a fourth aspect of the present invention, a cleaning and sterilization method for medical devices after use comprises the steps of:

performing a pre-cleaning process for removing a physical substance such as blood, mucus or tiny pieces of tissue that are attached to the exterior of the medical device and are inside a duct or a hollow portion;

immersing the pre-cleaned medical device in a chlorine dioxide solution and/or passing a chlorine dioxide solution through the duct or the hollow portion;

placing the medical device in a chlorine dioxide gas atmosphere and/or passing a chlorine dioxide gas through the duct or the hollow portion, so that the exterior of the medical device and the interiors of the duct and the hollow portion are deodorized, disinfected and sterilized.

According to the present invention, a chlorine dioxide solution that is supplied from a stabilized chlorine dioxide solution tank 10 to a container 16 for receiving a medical device can be a stabilized chlorine dioxide solution that is activated by ultraviolet irradiation or by the use of an acid product. In this case, multiple nozzles that communicate with a duct or a hollow portion of the medical device are provided at a proper locations along a pipe extending from a pressurization tank, such as a chlorine dioxide solution tank. When the duct or the hollow portion of the medical device that has been used is cleaned or disinfected by connecting one end thereof to the nozzles (tube current method), the duct or the hollow portion can be completely deodorized, disinfected and sterilized.

A chlorine dioxide gas, which is fed from a chlorine dioxide gas supplying device 20 into a container 16 for receiving a medical device, can be a stabilized chlorine dioxide solution or a gel thereof that is generated by ultraviolet irradiation or by a chemical reaction with an acid product. A chlorine dioxide gas supplied from the chlorine dioxide gas supplying device 20 can be set to circulate between the supplying device 20 and the container 16 for receiving the medical device.

In this case, multiple nozzles that communicate a duct or a hollow portion of a medical device are provided at proper locations along a pipe extending from the chlorine dioxide solution supplying device 20. When the duct or the hollow portion of the medical device that has been used is cleaned or disinfected by connecting one end thereof to the nozzles (tube current method), the duct or the hollow portion can be completely deodorized, disinfected and sterilized. In addition, a chlorine dioxide gas or a mixture of a chlorine dioxide gas or a carbon dioxide gas can be employed as a deodorization and sterilization gas.

In this invention, in order to repetitively employ various types of medical devices, such as endoscopes, arthoroscopes, catheters and tubes, that include ducts or hollow portions, a chlorine dioxide solution and a chlorine dioxide gas that provide superior sterilization effects can be employed as cleaning, deodorization and sterilization agents to efficiently perform a cleaning, drying and disinfection process within a short period of time, so that medical accidents, such as HBV (B-type hepatitis virus), C-type hepatitis virus or AIDS virus infections, for example, can be avoided.

It is preferable that the density of a chlorine dioxide solution used for the invention be 50 ppm to 1200 ppm, and more preferably around 100 ppm to about 150 ppm, and that the pH be 5 or less and preferably 4 or less. In addition, it is preferable that the density of a chlorine dioxide gas used for the invention be 5 ppm to 1000 ppm, and more preferably, around 10 ppm to about 300 ppm.

An ultrasonic vibrator can be added inside the container for a chlorine dioxide solution, and when ultrasonic vibration is applied, together with a jet of the solution or the circulating flow of the solution, the efficiency of the generation of chlorine dioxide can be increased, and unsanitary material attached to the medical device can be efficiently removed. It is convenient for the output of the ultrasonic generator to be variable in accordance with the target device to be cleaned, deodorized and sterilized, regardless of the generator type. Then, when the thus obtained chlorine dioxide solution is circulated and chlorine dioxide gas contacts the device, the device will be thoroughly cleaned and sterilized. A medical device, especially one having a long duct or hollow portion or an inside portion having a complicated shape, can be satisfactorily cleaned.

According to the invention, a cleaning and drying process using detergent water can be performed when a chlorine dioxide solution is discharged, and aeration processing can be performed when a chlorine dioxide gas is discharged from a duct or a hollow portion. In addition, the cleaning and drying processes using detergent water can also be performed after the exterior of a medical device and the inside of its duct or hollow portion have been cleaned, disinfected and sterilized.

Moreover, a chlorine dioxide gas may be employed by itself as a gas for deodorization, disinfection and sterilization. Or a chlorine dioxide gas and a carbon dioxide gas mixture may be sprayed directly on a target to be deodorized and sterilized, and/or may be discharged into a desired space wherein the target has been deposited. While chlorine dioxide gas and carbon dioxide gas both can provide effective deodorization, disinfection and sterilization, mixing these gases provides a synergistic effect. It should be noted that in this invention a container for a chlorine dioxide solution and a container for a chlorine dioxide gas can both be employed.

According to the present invention, a chlorine dioxide gas and/or a chlorine dioxide gas and a carbon dioxide gas mixture is injected into a gas cleaning and sterilization container, and this gas is passed through a duct or the container. As a result, deodorization, disinfection and sterilization can be effectively performed not only for the exterior of a medical device deposited in the container, but also for a duct or a hollow portion in the medial device.

Further, according to the thus organized medical device cleaning and sterilization method of this invention, a more complete deodorization, disinfection and sterilization process is performed within a shorter period of time, compared with the conventional cleaning and sterilization method. Therefore, serious medical accidents, such as infections caused by bacteria or viruses have not been removed, can be prevented.

Furthermore, an ozone generator can be additionally provided near the gas distribution outlet in the chlorine dioxide gas container, so that the sterilization effect can be improved. And in addition, in this invention an adverse environmental effect is eliminated by additionally providing means for absorbing a deleterious component of the chlorine dioxide gas, fed through the sterilization gas supply device, after it has passed through a target medical device to be deodorized and sterilized and is exhausted.

DETAILED DESCRIPTION OF THE PREFERRED EMBODIMENT

The preferred embodiment of the present invention will now be described in detail while referring to the accompanying drawings.

Figure 1:
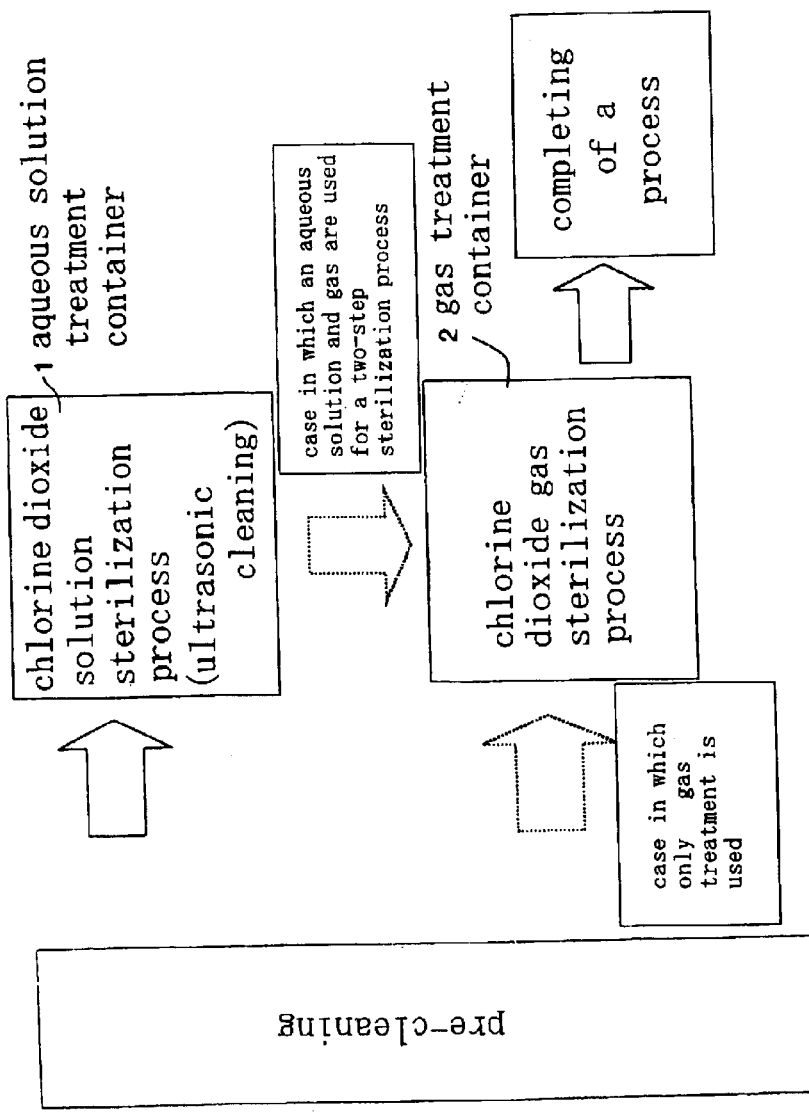
FIG. 1 is a block diagram showing a method for cleaning and sterilizing a medical device after use according to one embodiment of the present invention.

FIG. 1 is a diagram showing an example basic configuration, according to the present invention, for a method for cleaning and sterilizing a medical device after use.

A chlorine dioxide solution treatment container 1, which is conceptually shown in FIG. 1, is filled with a solution that is adjusted to a density of 100 ppm to 150 ppm and to a pH of about 4, and that is supplied from a pressurization tank, such as a chlorine dioxide sterilization solution tank. The solution treatment container 1 is constructed so that it is large enough for a medical device to be cleaned, deodorized and sterilized to be fully immersed in the solution. Further, it is convenient for a device for circulating a solution, such as an agitator, a circulating pump or a jet nozzle, to be provided for the solution treatment container 1. An ultrasonic vibrator is additionally provided for the inner wall or the bottom of the container 1, and is employed as needed. The material used for the container 1 is not especially limited; however, stainless steel, which provides superior corrosion resistance, is an appropriate material, although hard glass or porcelain may also be employed.

Multiple connection nozzles are formed for the pipe leading from the pressurization tank, located upstream of the solution treatment container 1, so that one end of a duct (channel) or a hollow portion in a medical device can be connected to the pipe. To clean and sterilize the duct or the hollow portion of the medical device, a jet of a pressurized, sterilized chlorine dioxide solution is fed to the tank and through the nozzles, and is discharged from the other end of the duct or the hollow portion. In this manner, the cleaning and sterilization of the interior is performed. Through the flow of the chlorine dioxide solution, and the synergistic effect produced by the jet and ultrasonic vibration, provided as needed, the exterior of the medical device and the inside of the duct can be completely cleaned and sterilized.

In this case, the time allocated for the cleaning and sterilization is appropriately set, depending on the target medical device, and it is preferable that the condition wherein the solution treatment container 1 is filled with a chlorine dioxide solution be maintained for from five to ten minutes. Then, when the employed solution is discharged from the container 1, the container 1 can also be used as a chlorine dioxide gas treatment container for two-step processing, i.e., the solution treatment and gas sterilization. When the same container is employed to perform gas sterilization using a chlorine dioxide gas, the cleaning and sterilizing process is performed by using the solution for a predetermined period of time, the solution is discharged from the solution treatment container 1, and a chlorine dioxide gas is rapidly supplied to perform gas sterilization. When a gas treatment container is employed separately from the solution treatment container to perform chlorine dioxide gas sterilization, as is indicated by a downward arrow in FIG. 1, a medical device from which water droplets are to be removed is moved to a chlorine dioxide gas treatment container 2. To perform gas sterilization, a chlorine dioxide gas that is adjusted to a density of 10 ppm to 300 ppm is appropriate. As a result, the sterilization and disinfection can be precisely performed, especially for a duct or a hollow portion that tends not to be uniformly disinfected merely by using a solution for the cleaning and sterilization.

A chlorine dioxide gas is supplied from the chlorine dioxide gas supplying device 20 so that it can circulate between the supplying device 20 and the treatment container 2 (or 1). Multiple connection nozzles to be connected to one end of a duct or to a hollow portion of a medical device are provided along the pipe extending from the chlorine dioxide gas supplying device 20, located upstream of the chlorine dioxide gas treatment container 2. The duct or tube shaped hollow portion of the medical device is connected to the nozzles, and a circulating flow of chlorine dioxide gas, fed by the gas supplying device 20, passes through the nozzles to deodorize, disinfect and sterilize the duct or the hollow portion of the medical device. The chlorine dioxide gas is discharged from the other end of the duct or the hollow portion and fills the gas treatment container 2, so that the exterior of the medical device can also be completely cleaned and sterilized.

Since the gas treatment container 2 includes a pressure controller and a heater, the internal pressure and the temperature can be adjusted as needed. And the desired states of a chlorine dioxide gas and another, added gas, internally supplied, can be maintained by the internal pressure provided by the gas treatment container 2, and the pressure of the discharged gas can be controlled by adjusting the heater temperature. For example, the heater temperature can be set to 80 to 100° C. and the pressure can be set to about 4 to 5 kg/m$^2$.

The mixing ratio for a chlorine dioxide gas and a carbon dioxide gas that are supplied to the container 2 can be adjusted within a wide range, such as 5:95 to 95:5, and can be changed depending on the target device to be deodorized, disinfected and sterilized. Therefore, a gas mixture supplied in this manner is a carbon dioxide gas (carbonate gas) or mist containing chlorine dioxide at the temperature of about 30 to 50° C.

Satisfactory effects can generally be obtained by supplying a gas at a density of about 10 ppm to 300 ppm; however, in a special case, the density can also be adjusted within a wider range.

In this embodiment, a chlorine dioxide gas and a chlorine carbon gas are supplied through pipes from the gas supplying device 20 to the gas treatment container 2, and by controlling the pressure and/or the temperature, a gas mixture (chlorine dioxide gas and carbon dioxide gas) or only a chlorine dioxide gas is supplied at a predetermined density. When a one-step process using chlorine dioxide gas is sufficient to sterilize a medical device that has been pre-cleaned, as is shown by a transverse, broken-line arrow the processing need only proceed directly from the pre-cleaning block to the gas sterilization process.

A target medical device is first pre-cleaned by a neutral detergent or by another appropriate detergent. For the cleaning to be performed satisfactorily, it is preferable that adhering substances, such as blood or mucus and proteins, be removed from the exterior of the device, and that a duct or a hollow portion of a device be cleaned using a benzalkonium chloride solution or a glutaral solution. For cleaning a lens portion it is more preferable to wipe it with a lens cleaner. The thus obtained medical device is placed in the chlorine dioxide solution treatment container 1, and is cleaned, deodorized, disinfected and sterilized by supplying the jet or the eddy current of the solution and a ultrasonic vibration.

The cleaning using a chlorine dioxide solution is performed for a period of time that is set in advance in accordance with the medical device type and the degree of contamination. While the density of the solution can also be set within a wide range, it should be selected in accordance with the medical device type and the diameter or the length the duct or the hollow portion of the medical device. Generally, an appropriate density for the solution is 100 ppm to 150 ppm.

Figure 2:
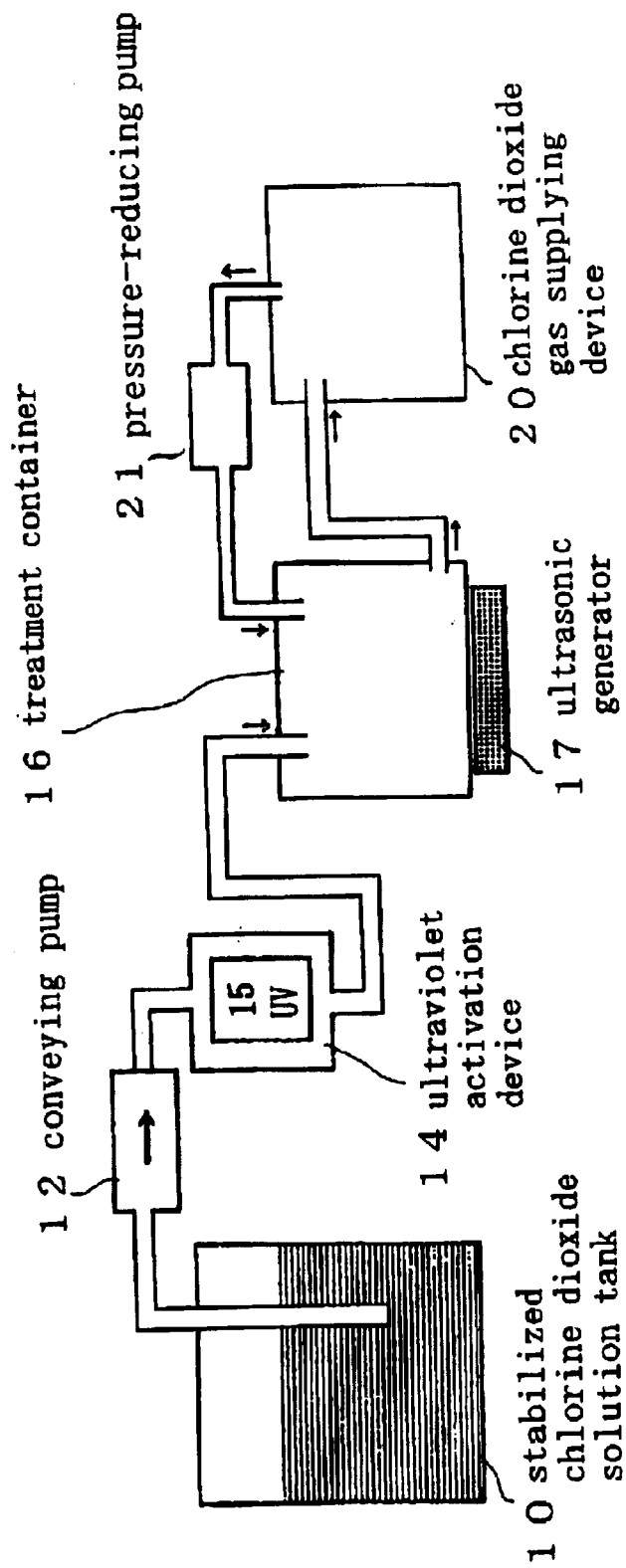
FIG. 2 is a diagram showing an example configuration, according to the present invention, for an apparatus for generating a chlorine dioxide solution and a chlorine dioxide gas employed for a method for cleaning and sterilizing a medical device after use.

FIG. 2 is a diagram showing an example configuration for an apparatus for generating a chlorine dioxide solution and a chlorine dioxide gas used for the method according to the invention for cleaning and sterilizing a medical device. A stabilized chlorine dioxide solution stored in a tank 10 is fed by a conveying pump 12 to an ultraviolet activation device 14 for activating a sterilized chlorine dioxide solution. An airtight ultraviolet irradiation lamp UV 15, which can be turned on in an aqueous solution, is provided for the ultraviolet activation device 14, and when the sterilized chlorine dioxide solution passes around the lamp 15, the sterilized chlorine dioxide solution is activated. The configuration in this embodiment is appropriate for continuous treatment. But it should be noted that various methods can be used for the activation process, which can also be performed chemically.

The thus activated chlorine dioxide solution is supplied to a chlorine dioxide solution or chlorine dioxide gas treatment container 16 (the aqueous solution treatment container or the gas treatment container in FIG. 1), and the solution is used for cleaning, disinfecting and sterilizing. It should be noted that the cleaning, disinfecting and sterilizing can be promoted when heat is generated by a heater (not shown) and an ultrasonic vibration is generated by an ultrasonic generator 17.

The chlorine dioxide solution in the treatment container 16 is supplied to the chlorine dioxide supplying device 20, and the chlorine dioxide gas is rapidly supplied by the supplying device 20 to the container 16, wherein the pressure is reduced by a pressure-reducing pump 21. In this atmosphere, gas sterilization is performed for the medical device.

Figure 3:
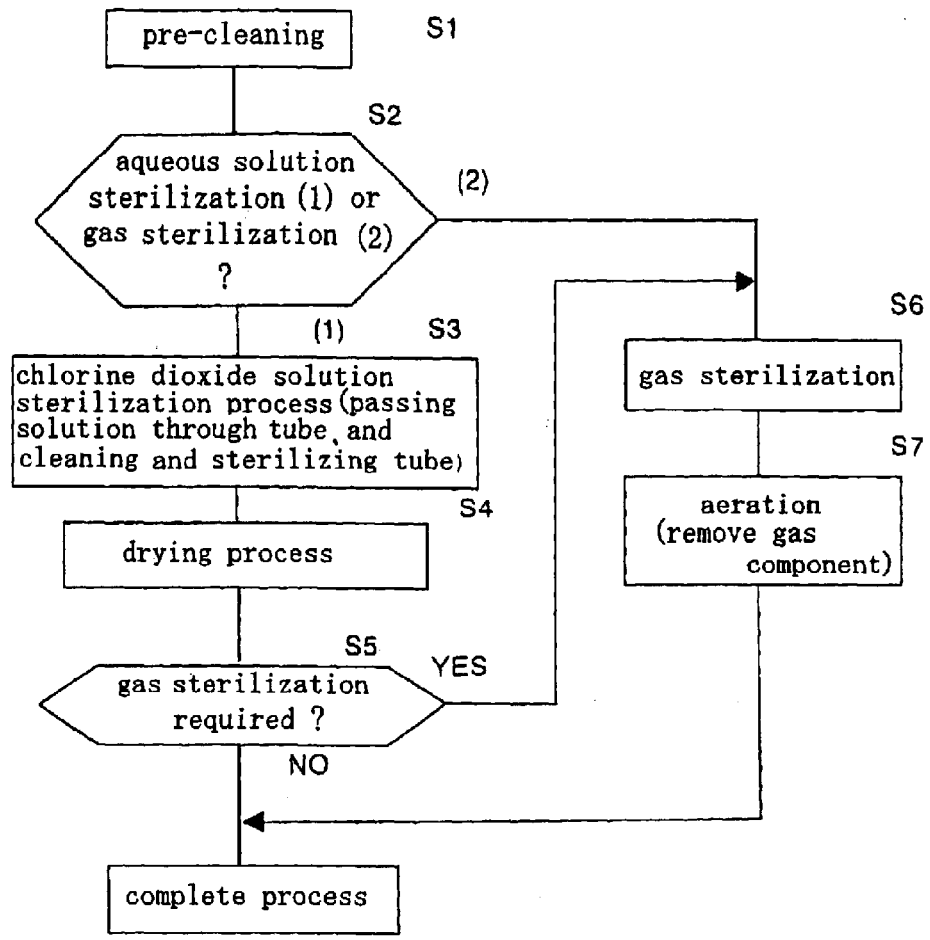
FIG. 3 is a flowchart showing the processing sequence, according to the present invention, performed by the method employed for cleaning and sterilizing a medical device after use.

FIG. 3 is a flowchart showing the processing sequence for the method, according to the present invention, for cleaning and sterilizing a medical device after use. First, the medical device is pre-cleaned to remove blood, mucus and pieces of human tissue that were attached to the exterior of the device when it was introduced into a human body (step S1).

For the pre-cleaning process, it is required that the detergent, the cleaning medium and the auxiliary cleaning tool that are designated by the maker of the medical device be employed to prevent defects, such as external damage, degeneration or malfunctions. For example, for a plastic member, a neutral detergent is mixed with tepid water and is used with a soft sponge to clean the outer surface of the plastic member. Further, it is also preferable that the interior of a duct, a pipe or a recessed portion be cleaned as thoroughly as possible by using compressed air, by flushing it out with water under pressure, by washing it with a brush, and, if available, by using ultrasonic vibration cleaning.

Then, a check is performed to determine whether a solution sterilization process (1) or a gas sterilization process (2) should be performed using a chlorine dioxide solution ($ClO_2$) (step S2). The reference for this determination is the type, the structure and the contaminated condition of the medical device. For the solution sterilization process (1), the solution treatment container 16 is filled with a chlorine dioxide solution, and the medical device is immersed in the solution to clean and sterilize the exterior of the device. In this case, it is preferable that the solution be passed through the tube-shaped portion to clean and sterilize the interior. For solution sterilization, a timing, ranging from two to ten minutes, need only be selected that is appropriate for the type of medical device. In this case, in accordance with the type of medical device, heating and the application of ultrasonic vibration may also be taken into account.

When in accordance with predetermined procedures, the cleaning and sterilization of a medical device, performed for a predetermined period of time, has been completed and, when required, a rinsing process (cleaning using detergent water) has been performed, a drying process is performed (step S4) for which the period, about ten minutes is sufficient, is determined in accordance with the type of medical device and the intricacy of the structure and the materials of the components of the device. Then, a check is performed to determine whether the gas sterilization process (2) using a chlorine dioxide gas should be performed (step S5). When it is ascertained that the gas sterilization process is not required because in accordance with the type and structure of the pertinent medical device the solution sterilization has been satisfactory, the processing for this invention is terminated.

When, however, it is initially determined at step S2 that the gas sterilization process (2) is required, or when it is ascertained at step S5, after the solution sterilization has been completed, that the gas sterilization is required, the gas sterilization is performed by filling the gas treatment container 16 with chlorine dioxide gas (step S6). During the gas sterilization process, since the gas treatment container 16 is filled with chlorine dioxide gas, not only the exterior of the medical device but also the interior of the tube-shaped portion can be sterilized. When the tube portion is narrow or long, however, to thoroughly sterilize the interior a gas discharge nozzle must be connected to the duct or to the hollow portion.

Next, aeration (a gas removal process) is performed to completely exhaust the gas in the duct or the hollow portion that has been sterilized (step S7). When it is ascertained, however, that aeration is not required because of the type and structure of the medical device, this process can be eliminated.

EXAMPLE 1

Disclosed are the results provided by a test conducted to examine the disinfection and sterilization effects obtained when a previously contaminated medical device (an OES upper digestive tract general-purpose fiberscope: an endoscope) was cleaned and sterilized using a chlorine dioxide solution.

(Test Purpose: Microbiological Verification of the Effects Obtained When Using Chlorine Dioxide to Disinfect an Endoscope)

test material . . . chlorine dioxide solution 500 ppm (product of Kabushiki Kaisha Sunseal)

device tested . . . OES upper digestive tract general purpose fiberscope (endoscope) (product of Olympus Optical Co., Ltd.)

test strain . . . Staphylococcus aureus ATTC 25923. . . *Escherichia coli* ATTC 25922 culture medium . . . SCDLP agar culture medium (Eiken Chemical Co., Ltd.) Lot. 28005 . . . SCDLP bouillon culture medium (Eiken Chemical Co., Ltd.) Lot. 28003

Adjustment of Test Bacteria Suspension

By using a sterilizing balanced saline solution, a test strain was adjusted so it had the turbidity of McFarland No. 1, and the resultant strain was employed as an inoculated bacteria suspension.

Testing Method (1) The distal end of the endoscope was covered with Parafilm, and a sterilization pipet was used to inject 1.5 ml of the test bacteria through a forceps opening. After the endoscope had not been disturbed for five minutes, it was determined that the interior of the forceps channel was contaminated.

(2) The distal end of the endoscope was opened, and the interior of the forceps channel was cleaned by the injection through the forceps opening of 2000 ml of detergent water. After the cleaning was started, 100 ml of solution was employed to obtain a bacteria number count.

(3) Using an air pump, compressed air was introduced at the forceps opening for ten minutes at a rate of 2000 ml/min.

(4) The endoscope was again cleaned using 100 ml of sterilizing water, and this cleaning water was employed to obtain a bacteria number count.

(5) The inside of the forceps channel was contaminated using the same method as in (1).

(6) The distal end of the forceps channel was opened and the inside of the channel was cleaned for 15 minutes by injecting 2000 ml of a chlorine dioxide solution through the forceps opening. After the cleaning was started, 100 ml of the solution was employed to obtain a bacteria number count.

(7) A chlorine dioxide gel was irradiated by an ultraviolet beam emitted by a UV lamp in order to promote vaporization. Using a pump, for ten minutes the generated chlorine dioxide gas was introduced through the forceps opening at a rate of 2000 ml/min.

(8) The forceps channel was cleaned again using 100 ml of sterilizing water, and the cleaning water was employed to obtain a bacteria number count.

Counting the number of bacteria and the culture conditions (1) Staphylococcus membrane filtermethod conforming ti the Japanese pharmacopoeia using an SCDLP agar medium petri-plate method conforming to the Japanese pharmacopoeia using the SCDLP agar medium increased bacteria culture for which a sample of 10 ml eas used to inoculate 10 ml of SCDLP bouillon having a double density aerobic culturing for three dyas at 36° C. using these methods (2) Escherichia coli membrane filtermethod congorming to the Japanese pharmacopoeia using an SCDLP agar medium petri-plate method conforming to the Japanese pharmacopoeia using the SCDLP agar medium inclreased bacteria culture for which a sample of 10 ml was used to inoculate 10 ml of SCDLP bouillon having a double density aerobic culturing for three days at 35° C. using these methods The results obtained from this test were as shown in Table 1.

TABLE 1

| Test bacteria type | *Escherichia coli* | *Staphylococcus aureus* |
|---|---|---|
| Density of inoculated bacteria suspension | 360,000,000 | 240,000,000 |
| Out of 2000 ml sterilizing water, 100 ml after cleaning was started | 280,000 | 310,000 |
| Sterilizing water, 100 ml (comparison) | 220 | 220 |
| Out of 2000 ml of clo2 solution, 100 ml after cleaning was started | Did not grow | Did not grow |
| Sterilizing water, 100 ml (sample) | Did not grow | Did not grow |

Since the growth of cultured bacteria was not detected following the cleaning and sterilization using a chlorine dioxide solution, following the cleaning and sterilization performed using chlorine dioxide gas a measurement was not conducted.

EXAMPLE 2

Disclosed are the results provided by a test conducted to examine the disinfection and sterilization effects obtained when a previously contaminated medical device (an OES upper digestive tract general-purpose fiberscope: an endoscope) was cleaned and sterilized using a chlorine dioxide gas.

(Test Purpose: Microbiological Verification of the Effects Obtained When Using a Chlorine Dioxide Gas to Disinfect an Endoscope)

test material . . . chlorine dioxide gel 20000 ppm (product of Kabushiki Kaisha Sunseal)

devices to be used . . . a chlorine dioxide gas generator for irradiating a chlorine dioxide gel with an ultraviolet beam emitted by a UV lamp and generating a chlorine dioxide gas (product of Kabushiki Kaisha Sunseal), a fumigating box (300 mm wide×450 mm deep×150 mm tall) (product of Kabushiki Kaisha Sunseal), and a sterilization dropping pipet No. 4 (product of Eiken Chemical Co., Ltd.)
device tested . . . OES upper digestive tract general purpose fiberscope (endoscope) (product of Olympus Optical Co., Ltd.)
test strain . . . *Staphylococcus aureus* ATTC 25923 . . . *Escherichia coli* ATTC 25922
culture medium . . . SCDLP agar culture medium (Eiken Chemical Co., Ltd.) Lot. 28005 . . . SCDLP bouillon culture medium (Eiken Chemical Co., Ltd.) Lot. 28003
Adjustment of Test Sample By using a sterilizing balanced saline solution, a test strain was adjusted to the turbidity of McFarland No. 1 and a resultant solution of 3 ml was sucked into a sterilization dropping pipet and was extracted to be contaminated. Then, the head of the solution was cut off to be employed as an inoculated bacteria suspension.
Test Method (1) The sample was placed in a fumigating box and closed. Then, a chlorine dioxide gas was introduced to fumigate the box and the box was not disturbed for one hour. For comparison, under the same conditions, a fumigating box that was not fumigated with chlorine dioxide gas was not disturbed for one hour.

(2) The fumigating box was cleaned using a phosphate buffer solution of 10 ml, and the number of bacteria in the cleaning solution was counted. The method used to count the number of bacteria was performed in the following manner. Counting the number of bacteria and the culture conditions (1) Staohylococcus aureua
  petri-plate method conforming to the Japanese pharmacopoeia using the SCDLP agar medium
  increased bacteria culture for which a sample of 10 ml was used to inoculate 10 ml of SCDLP bouillon having a double density
  aerobic culturing for three days at 35° C. using these methods (2) Escherichia coli
  petri-plate method conforming to the Japanese pharmacopoeia using the SCDLP agar medium
  increased bacteria culture for which a sample of 10 ml was used to inoculate 10 ml of SCDLP bouillon having a double density
  aerobic culturing for three days at 35° C. using these methods The results obtained from this test were as shown in Table 2.

The results obtained from this test were as shown in Table 2.

TABLE 2

| Test bacteria type | Escherichia coli | Staphylococcus aureus |
| --- | --- | --- |
| One hour after chlorine dioxide gas spraying | Did not grow | Did not grow |
| Comparison | 250,000 | 150,000 |

As is apparent from the test results, it is also proven microbiologically that the sterilization and disinfection effects can always be obtained when a test similar to the method of the invention is performed for an endoscope (gastrocamera) contaminated with Staphylococcus aureus and *Escherichia coli*.

According to method of the invention for the cleaning and sterilizing of a medical device, the medical device is sterilized using a chlorine dioxide solution and dried, is placed in the same container, or is moved to a separate gas treatment container as needed, and is deodorized, disinfected and sterilized using a chlorine dioxide gas. The method of the invention is especially effective for the deodorization, disinfection and sterilization of the outer surfaces of various types of medical devices, such as endoscopes, and the ducts or hollow portions of these devices. Further, the method of the invention is also highly effective for the prevention of a nosocomial infection.

In addition, after the gas sterilization is performed using the same container or a separate gas treatment container, the aeration process is performed as needed, and residual chlorine dioxide components can be completely removed. Further, depending on the device to be handled, an additional function, such as is provided by an ozone generator that effectively performs deodorization and sterilization, can also be employed.

As is described above, according to the method of the invention for the after use cleaning and sterilizing of medical devices, various types of endoscopes having long and narrow ducts or hollow portions, and medical tools, such as catheters and tubes, can be thoroughly deodorized, disinfected and sterilized. Thus, the risks associated with the contraction of various nosocomial infections, for example, can be eliminated, and safe and accurate examinations and operations can be performed.

Since it is obvious that many embodiments may be provided without departing from the scope of the present invention, the present invention is not limited to the above embodiment and is defined by the included claims.

What is claimed is:

1. A cleaning and sterilization method for medical devices after use comprising the steps of:
  performing a pre-cleaning process on a medical device to be introduced into a human body, for removing a physical substance such as blood, mucus or tiny pieces of tissue that are attached to the exterior of said medical device and are inside a duct or a hollow portion thereof;
  immersing said pre-cleaned medical device in a chlorine dioxide solution formed by an ultraviolet light being irradiated in a stabilized chlorine dioxide solution to liberate a chlorine gas having a sterilization effect and/or by adding an acid product, and passing said chlorine dioxide solution through said duct or said hollow portion;
  placing said processed medical device in a chlorine dioxide gas atmosphere formed by an ultraviolet light being irradiated in a stabilized chlorine dioxide gel in order to accelerate transpiring of said chlorine dioxide gas from said stabilized chlorine dioxide gel and/or by adding an acid product to the stabilized chlorine dioxide gel, and/or passing said chlorine dioxide gas through said duct or said hollow portion, so that the exterior of said medical device and the interiors of said duct and said hollow portion are deodorized, disinfected and sterilized.

2. A cleaning and sterilization method according to claim 1, wherein a tube current method for connecting one end of said duct or said hollow portion to a nozzle for a pressurized jet of the chlorine dioxide solution is employed in order to clean and/or deodorize, disinfect and sterilize said medical device.

3. A cleaning and sterilization method according to claim 2, wherein the density of said chlorine dioxide solution is 50 ppm to 1200 ppm, and the pH is 5 or less, and the density of said chlorine dioxide gas is 5 ppm to 1000 ppm.

4. A cleaning and sterilization method according to claim 3, wherein, during the processing at said steps, a drying process is performed when the chlorine dioxide solution is discharged, and aeration processing is performed when the chlorine dioxide gas is discharged from said duct or said hollow portion.

5. A cleaning and sterilization method according to claim 4, wherein cleaning and dying processes using detergent water are performed after the exterior of said medical device and the inside of said duct or said hollow portion have been cleaned, disinfected and sterilized.

6. A cleaning and sterilization method according to claim 2, wherein, during the processing at said steps, a drying process is performed when the chlorine dioxide solution is discharged, and aeration processing is performed when the chlorine dioxide gas is discharged from said duct or said hollow portion.

7. A cleaning and sterilization method according to claim 6, wherein cleaning and drying processes using detergent water are performed after the exterior of said medical device and the inside of said duct or said hollow portion have been cleaned, disinfected and sterilized.

8. A cleaning and sterilization method according to claim 2, wherein cleaning and drying processes using detergent water are performed after the exterior of said medical device and the inside of said duct or said hollow portion have been cleaned, disinfected and sterilized.

9. A cleaning and sterilization method according to claim 3, wherein cleaning and drying processes using detergent water are performed after the exterior of said medical device and the inside of said duct or said hollow portion have been cleaned, disinfected and sterilized.

10. A cleaning and sterilization method according to claim 1, wherein a tube current method for connecting one end of said duct or said hollow portion to a nozzle for a circulating jet of the chlorine dioxide gas is employed in order to clean and/or deodorize, disinfect and sterilize said medical device.

11. A cleaning and sterilization method according to claim 10, wherein the density of said chlorine dioxide solution is 50 ppm to 1200 ppm, and the pH is 5 or less, and the density of said chlorine dioxide gas is 5 ppm to 1000 ppm.

12. A cleaning and sterilization method according to claim 11, wherein, during the processing at said steps, a drying process is performed when the chlorine dioxide solution is discharged, and aeration processing is performed when the chlorine dioxide gas is discharged from said duct or said hollow portion.

13. A cleaning and sterilization method according to claim 12, wherein cleaning and drying processes using detergent water are performed after the exterior of said medical device and the inside of said duct or said hollow portion have been cleaned, disinfected and sterilized.

14. A cleaning and sterilization method according to claim 11, wherein cleaning and drying processes using detergent water are performed after the exterior of said medical device and the inside of said duct or said hollow portion have been cleaned, disinfected and sterilized.

15. A cleaning and sterilization method according to claim 10, wherein, during the processing at said steps, a drying process is performed when the chlorine dioxide solution is discharged, and aeration processing is performed when the chlorine dioxide gas is discharged from said duct or said hallow portion.

16. A cleaning and sterilization method according to claim 15, wherein cleaning and drying processes using detergent water are performed after the exterior of said medical device and the inside of said duct or said hollow portion have been cleaned, disinfected and sterilized.

17. A cleaning and sterilization method according to claim 10, wherein cleaning and drying processes using detergent water are performed after the exterior of said medical device and the inside of said duct or said hollow portion have been cleaned, disinfected and sterilized.

18. A cleaning and sterilization method according to claim 1, wherein the density of said chlorine dioxide solution is 50 ppm to 1200 ppm, and the pH is 5 or less, and the density of said chlorine dioxide gas is 5 ppm to 1000 ppm.

19. A cleaning and sterilization method according to claim 18, wherein, during the processing at said steps, a drying process is performed when the chlorine dioxide solution is discharged, and aeration processing is performed when the chlorine dioxide gas is discharged from said duct or said hollow portion.

20. A cleaning and sterilization method according to claim 19, wherein cleaning and drying processes using detergent water are performed after the exterior of said medical device and the inside of said duct or said hollow portion have been cleaned, disinfected and sterilized.

21. A cleaning and sterilization method according to claim 18, wherein cleaning and drying processes using detergent water are performed after the exterior of said medical device and the inside of said duct or said hollow portion have been cleaned, disinfected and sterilized.

22. A cleaning and sterilization method according to claim 1, wherein, during the processing at said steps, a drying process is performed when the chlorine dioxide solution is discharged, and aeration processing is performed when the chlorine dioxide gas is discharged from said duct or said hollow portion.

23. A cleaning and sterilization method according to claim 22, wherein cleaning and drying processes using detergent water are performed after the exterior of said medical device and the inside of said duct or said hollow portion have been cleaned, disinfected and sterilized.

24. A cleaning and sterilization method according to claim 1, wherein cleaning and drying processes using detergent water are performed after the exterior of said medical device and the inside of said duct or said hollow portion have been cleaned, disinfected and sterilized.

* * * * *